United States Patent [19]

Pavlin

[11] 4,310,714
[45] Jan. 12, 1982

[54] HYDROGENATION OF α-PINENE TO CIS-PINANE

[75] Inventor: Mark S. Pavlin, Lawrenceville, N.J.

[73] Assignee: Union Camp Corporation, Wayne, N.J.

[21] Appl. No.: 215,033

[22] Filed: Dec. 10, 1980

[51] Int. Cl.$^3$ .................. C07C 5/03; C07C 13/47
[52] U.S. Cl. .................. 585/275; 585/277; 585/350; 585/947
[58] Field of Search ............. 585/275, 947, 277, 350

[56] References Cited

U.S. PATENT DOCUMENTS

| | | | |
|---|---|---|---|
| 4,018,842 | 4/1977 | Cavova | 585/947 |
| 4,204,080 | 5/1980 | Bledsoe et al. | 585/273 |
| 4,261,927 | 4/1981 | Drake | 585/277 X |

OTHER PUBLICATIONS

Berkowitz and Rylander, J. Org. Chem., 24, 708, (1959).

Primary Examiner—Delbert E. Gantz
Assistant Examiner—G. E. Schmitkons
Attorney, Agent, or Firm—Kane, Dalsimer, Kane, Sullivan and Kurucz

[57] ABSTRACT

Ruthenium has been found to be a stereoselective catalyst for the hydrogenation of α-pinene to obtain cis-pinane.

13 Claims, No Drawings

HYDROGENATION OF α-PINENE TO CIS-PINANE

BACKGROUND OF THE INVENTION

1. Field of the Invention

The invention relates to the hydrogenation of unsaturated terpenes and more particularly relates to the selective hydrogenation of α-pinene to obtain cis-pinane.

2. Brief Description of the Prior Art

Representative of the prior art is the disclosure found in U.S. Pat. No. 4,018,842. This patent discloses the selective hydrogenation of α-pinene to obtain cis-pinane, employing as the hydrogenation catalyst a partially poisoned nickel catalyst. Although good selectivity of hydrogenation is achieved by the prior art process, the catalyst preparation is not without problems and frequent replacement of spent catalyst is required for subsequent hydrogenations. Furthermore, the most selective hydrogenations required impractically long times (up to 64 hours) for complete reaction.

By the method of my invention, a simple, commercially available compound or composition may be employed as the catalyst and the used catalyst re-used a plurality of times without further treatment or rejuvenation, particularly in the absence of catalyst poisons.

SUMMARY OF THE INVENTION

The invention comprises a method of preparing cis-pinane, which comprises; hydrogenating α-pinene in the presence of a catalytic proportion of ruthenium. A catalytic proportion is one which will promote the desired hydrogenation. In general, a catalytic proportion will be one within the range of from about 0.01 to about 10 percent by weight of the starting α-pinene; preferably about 0.05 to about 1.0 percent by weight.

An advantage of the invention resides in the high activity of relatively small quantities of the catalyst in comparison to, for example, nickel catalysts.

DETAILED DESCRIPTION OF THE INVENTION

The α-pinene hydrogenation reaction may be illustrated by the schematic formula:

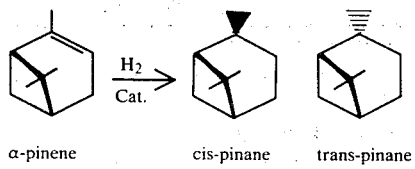

α-pinene     cis-pinane     trans-pinane

Advantageously, the hydrogenation is carried out under conditions which favor formation of the cis-isomer of pinane over the trans-isomer. Factors influencing or promoting such stereoselectivity include, for example, the hydrogenation catalyst and the hydrogenation pressure, temperature and reaction time. In general, lower temperatures, higher pressures and longer reaction times favor production of cis-pinane from α-pinene.

The present invention resides in my finding that ruthenium is a catalyst which, when employed under conventional hydrogenation conditions, will promote the formation of cis-pinane from α-pinene over the corresponding trans-isomer when all other factors for stereoselectivity are maintained constant. The advantage of the method of the invention resides in the need for only small loadings of the catalyst and mild conditions to achieve complete reduction in a relatively short time.

The term "conventional hydrogenation conditions" as used herein means those hydrogenation conditions (except for catalyst material), previously known for the preparation of cis-pinane from α-pinene. In general, such conditions are as follows.

TEMPERATURES

The hydrogenation may be carried out at a temperature within the range of from about $-10°$ C. to about $150°$ C., preferably about $30°$ C. to $80°$ C. and most preferably about $50°$ C. Optimal temperatures however are dependent on the hydrogen pressures employed during the hydrogenation. In general, at lower temperatures higher pressures will be required to obtain optimum rates of hydrogenation.

PRESSURES

The hydrogen pressure employed in the method of the invention may be varied within the range of from about 1 to about 3,000 atmospheres, preferably from about 10 to 100 atmospheres. Higher pressures favor hydrogenation rate and stereoselectivity but increase the capital costs of the hydrogenation plant facility.

HYDROGENATION TIMES

Progress of the hydrogenation may be followed by an observation of the amount of hydrogen taken up by the hydrogenation reaction mixture. One may terminate the hydrogenation at the point where a desired theoretical quantity of hydrogen has been absorbed. In general, most hydrogenations are complete within 6 hours.

SOLVENT

Although not necessary, it may be advantageous to conduct the hydrogenation in the presence of an inert solvent for the reactants or product. The term "inert solvent" means a solvent which does not enter into or adversely affect the desired course of the hydrogenation. Representative of inert solvents which may be employed are hydrocarbon solvents such as n-heptane, toluene and the like. Solvents including water, acetic acid, methanol, ethanol and the like which are known to improve the performance of ruthenium catalyzed reductions may also be employed; see for example Berkowitz and Rylander, *J. Org. Chem.*, 24 708 (1959).

SEPARATION OF PRODUCT

The desired cis-pinane is readily separated from the hydrogenation reaction mixture employing conventional techniques. For example the mixture may be filtered to remove catalyst and solvent may be removed by distillation.

The ruthenium catalyst used in the method of the invention may be in the form of any of its reduced or nonreduced valence states. Preferably, however, a reduced valence state is employed for its higher level of activity in promoting the desired hydrogenation. It is preferred that the catalyst be of the pre-activated (that is, reduced during manufacture) type. The ruthenium catalyst may be employed in its elemental form alone or may be supported on any of the carriers conventionally employed for this purpose in preparing hydrogenation catalysts. Representative of such carriers are alumina, carbon, kieselguhr, bentonite, asbestos, silica gel and the like. Preferred as carriers are carbon and alumina.

The catalyst may be suspended with the α-pinene for hydrogenation employing conventional mixing apparatus and technique. It may be advantageous to maintain the catalyst in a homogeneous suspension in the reaction mixture during hydrogenation. This may be accomplished with conventional shaking or stirring means associated with the reaction vessel.

Following separation of the desired cis-pinane, the ruthenium catalyst may be recovered and re-used a plurality of times in subsequent hydrogenations of α-pinene, by merely washing the separated catalyst. Alternatively, the catalyst may be re-used simply by decanting a portion of the product pinane and charging fresh pinene feed, thus using residual pinane as reaction solvent.

α Pinene Feedstock

Ruthenium, like other hydrogenation catalysts, may be deactivated by contact with certain so-called "poisons". Representative of ruthenium poisons are compounds containing sulfur, nitrogen, phosphorus and the like. Accordingly, it is advantageous to employ α-pinene feedstocks in the method of the invention which are substantially free of catalyst poisons. Feedstocks contaminated with catalyst poisons may be treated by known and conventional techniques to render them substantially free of the poisons. The term "substantially free of catalyst poisons" as used herein means freedom from quantities of the catalyst poisons which would significantly deactivate catalytic proportions of the catalyst in a single hydrogenation run.

perature (circa 25° C.) and the overhead stirrer activated. After 3 hours the reaction mixture is removed and an aliquot analyzed by vapor phase chromatography. The analysis shows a mixture as follows: cis-pinane, 96.2%; trans-pinane, 2.2%; cis-camphane, 1.1% and trans-camphane, 0.5% (this represents a hydrogenation selectivity for cis- over trans-pinane of 97.8%).

EXAMPLE 2

A standard low-pressure bottle is charged with 100 parts of 98% α-pinene (Aldrich Chemical Company purified as in Example 1) and 1.7 parts of 5% ruthenium-on-carbon (Aldrich Chemical Company). The charge is shaken at room temperature (25° C.) and under a pressure of 60 psig hydrogen until the uptake of hydrogen ceases (40 mins.). The bottle is then opened, swept with inert gas (helium) and charged with a further portion of α-pinene feed (100 parts) without removal of any catalyst. This reaction mixture is then shaken as before under a pressure of 60 psig hydrogen until the reaction is complete (70 mins.). Again the bottle is charged with fresh α-pinene feed (100 parts) which is then reduced to a conversion of 82% after 90 mins. The average cis-pinane selectivity over trans-pinane for this series of reactions is found to be 97.4%.

EXAMPLE 3

Repeating the general procedure of Example 1, supra., a series of hydrogenation runs are made, varying the catalyst, proportion of catalyst, α-pinene feedstock, solvent, time, pressures and temperatures. The hydrogenation conditions and results are given in the Table below.

TABLE

| Catalyst | | Solvent | | Feed | Hydrogenation Conditions | | | Results | |
|---|---|---|---|---|---|---|---|---|---|
| Type[a] | Loading[b] | Type | Amount[b] | Type[c] | Press. (psig) | Time (h) | Temp. (°C.) | Conversion[d] | Selectivity[e] |
| A | 2.0 | none | | A | 60 | 16[f] | Room | 100 | 94.3 |
| A | 1.0 | none | | A | 60 | 3.5 | Room | 100 | 94.9 |
| A | 1.5 | none | | A | 200 | 4 | Room | 100 | 95.9 |
| B | 0.5 | none | | A | 200 | 6 | Room | 100 | 97.0 |
| B | 2.0 | ethanol | 300 | A | 60 | 5 | Room | 100 | 98.9 |
| C | 1.0 | methanol | 1000 | B | 400 | 0.5 | 50 | 98 | 98.1 |
| C | 0.06 | methanol | 270 | A | 200 | 2 | 85 | 100 | 98.4 |
| C | 1.1 | water | 27 | B | 200 | 2 | 75 | 98 | 94.5 |
| C | 0.86 | methanol | 250 | B | 200 | 2 | 60 | 68 | 95.7 |
| C | 0.26 | ethanol | 62 | C | 200 | 1 | 90 | 90 | 96.7 |
| C | 0.26 | methanol | 20 | C | 200 | 3.5 | 50 | 79 | 98.0 |
| C | 0.44 | methanol | 55 | A | 200 | 6 | 0 | 100 | 99.1 |

[a] A = Engelhard 5% Ru/Al$_2$O$_3$; B = Aldrich 5% Ru/C; C = Matthey Bishop pre-reduced 5% Ru/C.
[b] Weight percent on feed weight.
[c] A = commercial 95% α-pinene passed through Al$_2$O$_3$ before use; B = commercial 95% α-pinene used as received; C = commercial α-pinene treated to reduce the sulfur content to circa 2 ppm.
[d] Percentage of the α-pinene reacted.
[e] Selectivity = $\frac{\text{cis-pinane}}{\text{cis-pinane + trans-pinane}} \times 100\%$.
[f] Allowed to shake overnight.

The following examples describe the manner and the process of making and using the invention and set forth the best mode contemplated by the inventor of carrying out the invention but are not to be construed as limiting. All parts are by weight unless otherwise stated.

EXAMPLE 1

Commercial α-pinene (95% α-pinene, 2% β-pinene, 2% camphene and 1% unknowns) is percolated through activated alumina to remove polar impurities and then charged (100 parts) to the glass liner of a 500 ml Parr bomb along with 7 parts of 5% ruthenium-on-alumina (Engelhard Industries). After the liner is placed in the bomb and the bomb head secured the bomb is pressurized with hydrogen gas to about 200 psig at room tem- Those skilled in the art will appreciate from the data presented in the above Table, that ruthenium is a highly active catalyst for the stereoselective hydrogenation of α-pinene to obtain cis-pinane. Consequently, the catalytic proportion of ruthenium required for the desired hydrogenation may be unexpectedly low, i.e.; generally less than 1.0 percent by weight of the α-pinane feedstock. This is a significant difference from processes employing for example partially poisoned nickel catalysts. Such catalysts must be used in proportions of circa 2-3 percent by weight of the α-pinene to achieve a comparable rate and stereoselectivity; see U.S. Pat. No. 4,018,842. The advantage is economic. Of course, higher proportions of catalyst may be used in the process of the invention, but by doing so the economic advantage might be lost.

What is claimed:

1. A method of preparing cis-pinane, which comprises; hydrogenating α-pinene in the presence of a catalytic proportion of ruthenium.

2. The method of claim 1 wherein said ruthenium is supported on a carrier.

3. The method of claim 2 wherein the carrier is selected from the group consisting of alumina and carbon.

4. The method of claim 1 wherein said proportion is within the range of from about 0.01 percent to about 10 percent by weight of the α-pinene.

5. The method of claim 1 wherein hydrogenation is carried out under a hydrogen pressure of from about 1 to about 3,000 atmospheres.

6. The method of claim 1 wherein hydrogenation is carried out at a temperature of from about −10° C. to about 150° C.

7. The method of claim 1 wherein the α-pinene is in a solvent.

8. The method of claim 1 wherein the α-pinene is substantially free of catalyst poisons.

9. A semi-continuous process for preparing cis-pinane, which comprises the steps of;
hydrogenating α-pinene substantially free of catalyst poisons in the presence of a catalytic proportion of ruthenium;
separating the ruthenium from the resulting hydrogenation mixture;
subjecting the separated ruthenium to a wash; and
re-using the washed ruthenium in a subsequent hydrogenation of α-pinene.

10. The process of claim 9 wherein steps are repeated a plurality of times.

11. The process of claim 9 wherein separating is carried out by filtering the hydrogenation mixture.

12. A semi-continuous process for preparing cis-pinane, which comprises the steps of;
hydrogenating α-pinene substantially free of catalyst poisons in the presence of a catalytic proportion of ruthenium;
separating cis-pinane from the resulting hydrogenation mixture;
adding additional of said α-pinene to said hydrogenation mixture; and
hydrogenating the added α-pinene.

13. The process of claim 12 wherein steps are repeated a plurality of times.

* * * * *